United States Patent
Lopa

(10) Patent No.: US 10,272,360 B2
(45) Date of Patent: Apr. 30, 2019

(54) PHYTOCHEMICAL EXTRACTION SYSTEM AND METHODS TO EXTRACT PHYTOCHEMICALS FROM PLANTS INCLUDING PLANTS OF THE FAMILY CANNABACEAE SENSU STRICTO

(71) Applicant: Frank Augustino Lopa, Staten Island, NY (US)

(72) Inventor: Frank Augustino Lopa, Staten Island, NY (US)

(73) Assignee: Priya Naturals, Inc., Staten Island, NY (US)

(*) Notice: Subject to any disclaimer, the term of this patent is extended or adjusted under 35 U.S.C. 154(b) by 0 days.

(21) Appl. No.: 15/669,907

(22) Filed: Aug. 5, 2017

(65) Prior Publication Data

US 2017/0333809 A1    Nov. 23, 2017

(51) Int. Cl.
| | | |
|---|---|---|
| *A61K 36/185* | (2006.01) | |
| *B01D 7/00* | (2006.01) | |
| *C11B 1/12* | (2006.01) | |
| *G05B 15/02* | (2006.01) | |
| *B01D 3/38* | (2006.01) | |
| *B01D 11/00* | (2006.01) | |
| *B01D 3/10* | (2006.01) | |
| *C11B 1/10* | (2006.01) | |
| *C11B 9/00* | (2006.01) | |
| *A23L 33/105* | (2016.01) | |

(52) U.S. Cl.
CPC .............. *B01D 7/00* (2013.01); *A23L 33/105* (2016.08); *A61K 36/185* (2013.01); *B01D 3/10* (2013.01); *B01D 3/38* (2013.01); *B01D 11/00* (2013.01); *C11B 1/10* (2013.01); *C11B 1/12* (2013.01); *C11B 9/0003* (2013.01); *G05B 15/02* (2013.01); *A61K 2236/31* (2013.01); *A61K 2236/37* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| 1,679,728 A | 8/1926 | Lynn |
|---|---|---|
| 2,198,412 A | 4/1940 | McDonald |

(Continued)

FOREIGN PATENT DOCUMENTS

| EP | 1955749 A1 | 8/2008 |
|---|---|---|
| EP | 1385595 B2 | 5/2012 |

(Continued)

OTHER PUBLICATIONS

Abrams et al. (2007) Nature: Clinical Pharmacology and Therapeutics, vol. 82, No. 5, 572-578 (Year: 2007).*

(Continued)

*Primary Examiner* — Christopher R Tate
*Assistant Examiner* — Russell G Fiebig
(74) *Attorney, Agent, or Firm* — The Roy Gross Law Firm, LLC; Roy Gross

(57) ABSTRACT

A method and system of and for extraction or removal of phytochemicals from plants, including those of the plant family Cannabaceae sensu stricto. More specifically, a method and system for extracting essential oils from plants, such as *cannabis*, without the use of a solvent.

9 Claims, 11 Drawing Sheets

(56) References Cited

U.S. PATENT DOCUMENTS

| | | | |
|---|---|---|---|
| 2,414,418 A | 1/1947 | Lofton | |
| 2,908,614 A | 10/1959 | Muggleton | |
| 3,033,690 A | 5/1962 | Tarvin | |
| 3,219,461 A | 11/1965 | Lamb | |
| 3,238,736 A | 3/1966 | MacIntosh | |
| 3,270,437 A | 9/1966 | Lara | |
| 3,280,471 A | 11/1966 | Cole | |
| 3,289,314 A | 12/1966 | Porta | |
| 3,298,188 A | 1/1967 | Webster et al. | |
| 3,319,344 A | 5/1967 | Sachel et al. | |
| 3,401,466 A | 9/1968 | Brewster | |
| 3,438,792 A | 4/1969 | Kruger | |
| 3,871,190 A | 3/1975 | Harper et al. | |
| 3,936,489 A | 2/1976 | Rozsa et al. | |
| 4,279,824 A | 4/1981 | McKinney | |
| 4,554,170 A * | 11/1985 | Panzner | B01D 11/02 |
| | | | 426/651 |
| 4,574,495 A | 3/1986 | Brander | |
| 4,802,286 A | 2/1989 | Kobayashi | |
| 5,292,899 A | 3/1994 | Tius et al. | |
| 5,372,680 A | 12/1994 | Bezdolny et al. | |
| 5,467,612 A | 11/1995 | Venetucci | |
| 5,516,923 A | 5/1996 | Herbert et al. | |
| 5,525,746 A | 6/1996 | Franke | |
| 6,128,831 A | 10/2000 | Durance et al. | |
| 6,195,908 B1 | 3/2001 | Crul | |
| 6,350,351 B1 | 2/2002 | Popov et al. | |
| 6,354,301 B2 | 3/2002 | McCoy | |
| 6,361,813 B1 | 3/2002 | Kitaoka et al. | |
| 6,365,416 B1 | 4/2002 | Elsohly et al. | |
| 6,403,126 B1 * | 6/2002 | Webster | A61K 36/185 |
| | | | 424/725 |
| 6,715,494 B1 | 4/2004 | McCoy | |
| 6,730,519 B2 | 5/2004 | Elsohly et al. | |
| 6,946,150 B2 | 9/2005 | Whittle | |
| 7,025,992 B2 | 4/2006 | Whittle et al. | |
| 7,291,250 B1 | 11/2007 | Popp et al. | |
| 7,344,736 B2 | 3/2008 | Whittle et al. | |
| 7,402,686 B2 | 7/2008 | Duchek | |
| 7,521,079 B2 | 4/2009 | Sakai et al. | |
| 7,524,881 B2 | 4/2009 | Goodwin et al. | |
| 7,592,468 B2 | 9/2009 | Goodwin et al. | |
| 7,622,140 B2 | 11/2009 | Whittle et al. | |
| 7,700,368 B2 | 4/2010 | Flockhart et al. | |
| 7,826,726 B2 | 11/2010 | McCoy | |
| 8,106,244 B2 | 1/2012 | Burdick et al. | |
| 8,337,908 B2 | 12/2012 | Letzel et al. | |
| 8,343,553 B2 | 1/2013 | Hospodor | |
| 8,445,034 B1 | 5/2013 | Coles, Jr. | |
| 8,530,679 B2 | 9/2013 | Bhatarah et al. | |
| 8,673,368 B2 | 3/2014 | Guy et al. | |
| 8,846,409 B2 | 9/2014 | Flockhart et al. | |
| 8,859,793 B2 | 10/2014 | Hamler et al. | |
| 8,884,100 B2 | 11/2014 | Page et al. | |
| 8,895,078 B2 | 11/2014 | Mueller | |
| 8,906,956 B2 | 12/2014 | Rossi et al. | |
| 9,022,040 B2 | 5/2015 | Murphy | |
| 9,034,395 B2 | 5/2015 | Whittle et al. | |
| 9,035,130 B2 | 5/2015 | De Meijer | |
| 9,044,390 B1 | 6/2015 | Speier | |
| 9,095,554 B2 | 8/2015 | Lewis et al. | |
| 9,095,555 B2 | 8/2015 | Winnicki | |
| 9,155,767 B2 | 10/2015 | Hospodor et al. | |
| 9,186,386 B2 | 11/2015 | Speier | |
| 9,199,960 B2 | 12/2015 | Ferri | |
| 9,205,063 B2 | 12/2015 | Guy et al. | |
| 9,259,449 B2 | 2/2016 | Raderman | |
| 9,327,210 B1 | 5/2016 | Jones | |
| 9,333,229 B2 | 5/2016 | Bjorncrantz | |
| 9,333,441 B2 | 5/2016 | Gu et al. | |
| 9,340,475 B2 | 5/2016 | Mona, III et al. | |
| 9,351,953 B2 | 5/2016 | Stodola | |
| 9,358,259 B2 | 6/2016 | Hospodor et al. | |
| 9,565,865 B2 | 2/2017 | Bhairam | |
| 9,592,457 B2 | 3/2017 | Dabao | |
| 9,629,886 B2 | 4/2017 | Franklin et al. | |
| 9,649,349 B1 | 5/2017 | Tucker et al. | |
| 9,649,575 B2 | 5/2017 | Hopkins et al. | |
| 9,655,936 B2 | 5/2017 | Ruben et al. | |
| 9,655,937 B2 | 5/2017 | Jones | |
| 9,669,326 B2 | 6/2017 | Todosiev et al. | |
| 9,669,328 B2 | 6/2017 | Jones | |
| 2002/0039795 A1 | 4/2002 | Elsohly et al. | |
| 2002/0086438 A1 | 7/2002 | Elsohly et al. | |
| 2003/0017216 A1 | 1/2003 | Schimdt et al. | |
| 2003/0050334 A1 | 3/2003 | Murty et al. | |
| 2003/0229027 A1 | 12/2003 | Eissens et al. | |
| 2004/0033280 A1 | 2/2004 | Whittle | |
| 2004/0049059 A1 | 3/2004 | Mueller | |
| 2004/0138293 A1 | 7/2004 | Werner et al. | |
| 2004/0147767 A1 | 7/2004 | Whittle et al. | |
| 2004/0147769 A1 | 7/2004 | Davis | |
| 2005/0049298 A1 | 3/2005 | Goodwin et al. | |
| 2005/0266108 A1 | 12/2005 | Flockhart et al. | |
| 2006/0167283 A1 | 7/2006 | Flockhart et al. | |
| 2007/0212465 A1 | 9/2007 | Visram et al. | |
| 2008/0031977 A1 | 2/2008 | Musty et al. | |
| 2008/0103193 A1 | 5/2008 | Castor et al. | |
| 2008/0128261 A1 | 6/2008 | Balass | |
| 2008/0138486 A1 | 6/2008 | Jones | |
| 2008/0167483 A1 | 7/2008 | Whittle et al. | |
| 2009/0317523 A1 | 12/2009 | Hirschberg et al. | |
| 2010/0034935 A1 | 2/2010 | Wally et al. | |
| 2010/0034950 A1 | 2/2010 | Jones et al. | |
| 2010/0070108 A1 | 3/2010 | Kluetsch et al. | |
| 2010/0119606 A1 | 5/2010 | Whittle et al. | |
| 2010/0168448 A1 | 7/2010 | Flockhart et al. | |
| 2011/0039009 A1 | 2/2011 | Jones et al. | |
| 2011/0076378 A1 | 3/2011 | Jones et al. | |
| 2011/0100894 A1 | 5/2011 | Miller | |
| 2011/0133120 A1 | 6/2011 | McGhee | |
| 2011/0201836 A1 | 8/2011 | O'Lenick, Jr. | |
| 2011/0256245 A1 | 10/2011 | Rosenblatt et al. | |
| 2012/0183666 A1 | 7/2012 | Jones et al. | |
| 2012/0263804 A1 | 10/2012 | Hospodor | |
| 2013/0012575 A1 | 1/2013 | Letzel et al. | |
| 2013/0079531 A1 | 3/2013 | Barringer | |
| 2013/0149322 A1 | 6/2013 | Van Spronsen et al. | |
| 2013/0251824 A1 | 9/2013 | Hospodor et al. | |
| 2013/0256245 A1 | 10/2013 | Kuo et al. | |
| 2014/0113010 A1 | 4/2014 | Hospodor et al. | |
| 2014/0114084 A1 | 4/2014 | Hamler et al. | |
| 2014/0193456 A1 | 7/2014 | Dyanov et al. | |
| 2014/0248379 A1 | 9/2014 | Muellar | |
| 2014/0271940 A1 | 9/2014 | Wurzer | |
| 2014/0341934 A1 | 11/2014 | Van Spronsen et al. | |
| 2015/0044315 A1 | 2/2015 | Letzel et al. | |
| 2015/0105569 A1 | 4/2015 | Emo | |
| 2015/0119592 A1 | 4/2015 | Hamler et al. | |
| 2015/0126754 A1 | 5/2015 | Fernandez Cid et al. | |
| 2015/0203434 A1 | 7/2015 | Flockhart et al. | |
| 2015/0258153 A1 | 9/2015 | Rosenblatt et al. | |
| 2015/0297653 A1 | 10/2015 | Speier | |
| 2015/0297654 A1 | 10/2015 | Speier | |
| 2015/0375136 A1 | 12/2015 | Swan | |
| 2016/0022627 A2 | 1/2016 | Smith | |
| 2016/0038437 A1 | 2/2016 | Whittle et al. | |
| 2016/0074450 A1 | 3/2016 | Hospodor et al. | |
| 2016/0074451 A1 | 3/2016 | Speier | |
| 2016/0106705 A1 | 4/2016 | Verzura et al. | |
| 2016/0136541 A1 | 5/2016 | Jones | |
| 2016/0201009 A1 | 7/2016 | Lopez | |
| 2016/0213720 A1 | 7/2016 | Barringer | |
| 2016/0228787 A1 | 8/2016 | Payack | |
| 2016/0245588 A1 | 8/2016 | Baugh et al. | |
| 2016/0279183 A1 | 9/2016 | Hospodor et al. | |
| 2016/0287652 A1 | 10/2016 | Scott | |
| 2016/0324909 A1 | 11/2016 | Scialdone | |
| 2016/0326130 A1 | 11/2016 | Changoer et al. | |
| 2016/0331913 A1 * | 11/2016 | Bourque | A61M 11/02 |
| 2016/0346339 A1 | 12/2016 | Finley et al. | |
| 2016/0360721 A1 | 12/2016 | De Meijer | |
| 2017/0008870 A1 | 1/2017 | Dibble et al. | |
| 2017/0020943 A1 | 1/2017 | Raderman | |

(56) References Cited

U.S. PATENT DOCUMENTS

| | | |
|---|---|---|
| 2017/0020944 A1 | 1/2017 | Towle |
| 2017/0049830 A1 | 2/2017 | Raderman |
| 2017/0051231 A1 | 2/2017 | Mancosky |
| 2017/0106030 A1 | 4/2017 | Aari et al. |
| 2017/0119040 A1 | 5/2017 | Cameron |

FOREIGN PATENT DOCUMENTS

| | | |
|---|---|---|
| WO | 2002089945 A2 | 11/2002 |
| WO | 2016064987 A1 | 4/2016 |

OTHER PUBLICATIONS

Hazekamp et al. (2006) J. Pharmaceutical Sciences, vol. 95, No. 6, 1308-1317 (Year: 2006).*

Heath et al. (1994) J. Chemical Ecology, vol. 20, No. 3, 593-608 (Year: 1994).*

Lanz et al. (2016) PLoS ONE 11(1): e0147286. (Year: 2016).*

Pomahacova et al. (2009) Inhalation Toxicology 21(13): 1108-1112 (Year: 2009).*

Raskin et al. (2004) Current Pharmaceutical Design, 10, 3419-3429. (Year: 2004).*

Schmelz et al. (2004) The Plant Journal, 39, 790-808. (Year: 2004).*

Van der Kooy et al. (2008) Inhalation Toxicology, 20:9, 801-804. (Year: 2008).*

Nasshorudin et al., "Novel Closed System Extraction of Essential Oil : A Green Approach", American Journal of Biochemistry, Jan. 1, 2016 (Jan. 1, 2016), pp. 145-148.

Zhang et al, "Microwave assisted extraction of secondary metabolites from plants: Current status and future directions", Trends in Food Science and Technology, vol. 22, No. 12, Dec. 31, 2011, pp. 672-688.

International Search Report PCT/US2018/026862 Completed: Jul. 18, 2018; dated Jul. 27, 2018 5 pages.

Written Opinion of the International Searching Authority PCT/US2018/026862 dated Jul. 27, 2018 10 pages.

* cited by examiner

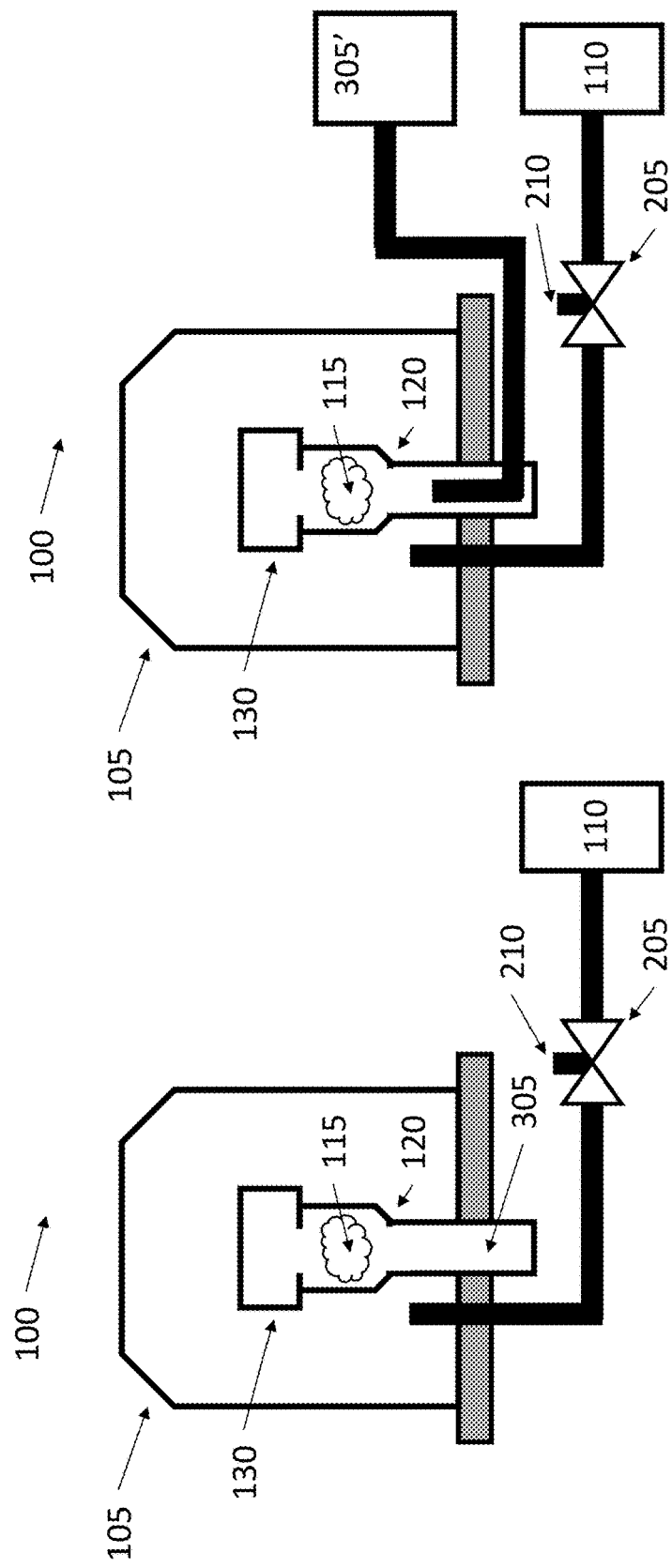

PHYTOCHEMICAL EXTRACTION SYSTEM AND METHODS TO EXTRACT PHYTOCHEMICALS FROM PLANTS INCLUDING PLANTS OF THE FAMILY CANNABACEAE SENSU STRICTO

FIELD OF THE INVENTION

The present invention is directed to advanced extraction systems and methods to extract or remove phytochemicals from plants, including those of the plant family Cannabaceae sensu stricto. The present invention is directed to plant oil extraction and, more specifically, the use of a method and system for extracting essential oils from plants, such as cannabis, without the use of a solvent.

BACKGROUND OF THE INVENTION

"In the beginning God made heaven and earth. . . . Then God said, Behold, I have given you every seed-bearing herb that sows seed on the face of all the earth, and every tree whose fruit yields seed; to you it shall be for food. I also give every green plant as food for all the wild animals of the earth, for all the birds of heaven, and for everything that creeps on the earth in which is the breath of life." It was so. Then God saw everything He had made, and indeed, it was very good. So evening and morning were the sixth day." Book of Genesis, Chap 1:1, 29-31, commonly attributed to "the Yahwist", circa 5th Century B.C.E, as translated and interpreted in The Orthodox Study Bible: Ancient Christianity Speaks to Today's World, Thomas Nelson Publishing, 2008, USA.

" . . . the greatest service which can be rendered to any country is to add a useful plant to its culture; especially a bread grain, next in value to bread, is oil.", Thomas Jefferson, 3rd President of the United States of America, Memorandum of Services to My Country, Sep. 2, 1800, Charlottesville, Va. USA.

Many plants, such as plants from the family Cannabaceae sensu stricto, have many medicinal and therapeutic activity and uses. The medicinal and therapeutic activity of plants is primarily due to the active biological compounds or phytochemicals that the plants contain. The activity of phytochemicals is typically associated to a specific plant species of which a combination of compounds act in concert or harmony to result in a healing or medicinal outcome. Regardless of the concentration in a phyto-biomass, it is desirable to extract specific compounds, or produce an enriched and/or purified extract from plants, which can be then used for medicinal and pharmaceutical formulations.

Known extraction methods and systems which have been used to separate phytochemicals from plants, and produce enriched compounds, include maceration, decoction, distillation, sublimation, and extraction with aqueous and non-aqueous solvents.

Maceration may be defined as the extraction of a compound in a solvent at ambient room temperature with daily shaking or stirring. After a selected period, the solid material is separated from the solution. Variation on the method includes agitation of the macerate and the use of temperatures up to approximately 50° C. A variation of the method includes preparation of tinctures and extracts from low-density plant materiel using various strengths of ethanol as a solvent.

Decoction has been used since antiquity for the preparation of medicines; and customarily in traditional Chinese medicine, to place the quantity of herbs required for one day's treatment into a vessel and add hot or boiling water. The vessel may be brought to a boil and allowed to simmer for one or more hours. Once cooled, solid particles are filtered out and the decoction administered orally.

Maceration and decoction rely on short path diffusion, where inactive constituents such as lecithins, flavonoids, glycosides and sugars act to solubilize compounds which, in a pure state, are soluble in the solvent. A disadvantage of maceration and decoction with water or low concentrations of ethanol is that a large quantity of inert material typically having no therapeutic value must be removed. This inert material may consist of plant cell elements including, but not limited to fats, waxes, carbohydrates, proteins, and sugars. This may contribute to microbiological spoilage of a resulting product if not used promptly or further refined or preserved in some fashion. If dried, such extracts tend to be hygroscopic and difficult to formulate. The inert material may also affect how active phyto-elements are absorbed in and from a finished formulation.

Maceration and decoction are still widely used in situations where convenience outweighs precise dosage accuracy. Macerate and/or percolate solvents may be removed by evaporation at temperatures below 100° C. dependent upon the solvent used.

A wide range of processes based on the use of non-aqueous solvents to extract compounds from plants are known and taught in the prior art. Solvents employed may be miscible or immiscible with water and vary in efficacy. Techniques used to extract compounds from plants include liquid and solid extraction, liquid and gas chromatography and other separation and fractioning techniques.

Traditionally, for plant materials, ethyl alcohol in various concentrations is used to extract active substances. Tinctures are ethanol solutions easily produced and well described in most major pharmacopoeias. Where the final concentration of alcohol is greater than approximately 20% by volume, the tincture remains microbiologically stable and widely used in compounding prescriptions. Ethanol extracts substances such as glycosides, flavonoids and alkaloid salts are examples of compounds known to be biologically active. Ethanol also extracts considerable amounts of plant pigment, such as chlorophyll and carotenoids. By using higher alcohol strengths, lipid-soluble material may be extracted. Tinctures typically contain less inert material than macerates or decoctions, but are still complex mixtures of plant chemical elements. Where alcohol is not required or desired, a tincture may be evaporated to produce ethanol free extracts.

Lipid solvents are also used to extract lipid soluble chemical elements from a phyto-biomass. Examples are chlorinated solvents such as dichloromethane, chloroform, carbon-tetrachloride, hexane, ether, fluorinated hydrocarbons, and supercritical fluid extraction with inert agents such as carbon dioxide.

Using chlorinated solvents is highly disadvantageous for phyto-biomass extraction because of extreme toxicity; and because for medicinal or pharmaceutical use such toxic solvents must be removed by various means before administration. Hexane and other petroleum-based solvents have good solvent activity; however, they must also be completely removed from any end product, and also carry the risk of fire and explosion during use.

Distillation and sublimation have been widely used to separate components of phyto-chemicals which have boiling points close to water (100° C.) at sea-level atmospheric pressure (14 psi). Chemical separation by distillation is widely used in the preparation of essential oils and also petrochemicals.

However, using at temperature at or above 100° C. to extract a phytochemical from plant material or a phytochemical composition is extremely undesirable and disadvantageous in many cases, as the temperature adversely affects or changes many phytochemicals and plant compounds. One process that results from using high temperatures is decarboxylation of plant material. Decarboxylation is a chemical reaction that removes a carboxyl group and releases carbon dioxide ($CO_2$). Usually, decarboxylation refers to a reaction of carboxylic acids, such as removing a carbon atom from a carbon chain.

In many instances, a phytochemical is desired and/or required in a "natural" form; therefore, eliminating from feasible use nearly all known extraction methods and systems which utilize heating or temperatures at or above 100° C.

Known methods and systems used to extract compounds include: U.S. Pat. Nos. 1,679,728, 2,198,412, 2,414,418, 3,270,437, 3,936,489, 4,279,824, 5,372,680, 5,516,923, 5,525,746, 6,350,351, 6,365,416, 6,403,126, 6,730,519, 6,946,150, 7,025,992, 7,291,250, 7,344,736, 7,524,881, 7,592,468, 7,622,140, 7,700,368, 8,343,553, 8,445,034, 8,530,679, 8,673,368, 8,846,409, 8,859,793, 8,895,078, 8,906,956, 9,022,040, 9,034,395, 9,034,395, 9,035,130, 9,044,390, 9,186,386, 9,199,960, 9,205,063, 9,327,210, 9,333,441, 9,358,259, 9,592,457, 9,649,349, 9,649,349, 9,649,575, 9,655,936, 9,655,937, 9,669,326, 9,669,328, US20020039795, US20020086438, US20030017216, US20030050334, US20040033280, US20040049059, US20040147767, US20040147769, US20050049298, US20060167283, US20080031977, US20080167483, US20100119606, US20100168448, US20110100894, US20110133120, US20110201836, US20110256245, US20120263804, US20130079531, US20130149322, US20130256245, US20120263804, US20130079531, US20130149322, US20130251824, US20140113010, US20140114084, US20140248379, US20140341934, US20150105569, US20150119592, US20150203434, US20150258153, US20150297653, US20150297654, US20150375136, US20160038437, US20160074450, US20160074451, US20160106705, US20160136541, US20160201009, US20160136541, US20160201009, US20160213720, US20160228787, US20160279183, US20160324909, US20160326130, US20160346339, US20160360721, US20170008870, US20170020943, US20170020944, US20170049830, US20170051231, US20170106030, US20170119040.

It is desired to provide a method and system to overcome the above-mentioned and other disadvantages in the prior art by and for removing phytochemicals and plant compounds from plant material or a phytochemical composition without adversely or undesirably by heat affecting the extracted phytochemicals themselves.

It is desired to provide a method and system that overcomes the above-mentioned and other disadvantages in the prior art and by and for removing phytochemicals from plant material or phytochemical compositions from the plant family Cannabaceae sensu stricto without adversely or undesirably by heat affecting the extracted phytochemicals themselves.

SUMMARY OF THE INVENTION

It is an object of the present invention to provide a method and system of and for extracting or separating a phytochemical from plant material or a phytochemical composition.

It is an object of the present invention to provide a method and system of and for extracting or separating a phytochemical from plant material or a phytochemical composition without utilizing a solvent.

It is an object of the present invention to provide a method and system of and for extracting or separating a phytochemical from plant material or a phytochemical composition without utilizing heat or temperatures at or above 100° C.

While not wishing to be bound by any one theory or combination of theories, it is believed and proven by instant inventor experimentation that utilizing at least a partial vacuum to reduce the temperature at which a phytochemical volatizes and/or precipitates from plant material or a phytochemical composition may be used to collect one or more phytochemicals, which can be used for medical, industrial, and scientific purposes.

While not wishing to be bound by any one theory or combination of theories, it is believed and proven by instant inventor experimentation that utilizing at least a partial vacuum to reduce the temperature at which a phytochemical volatizes and/or precipitates from plant material or a phytochemical composition may be used to collect one or more phytochemical, without causing substantial undesired alteration and/or degradation of the extracted phytochemical, which can be used for medical, industrial, and scientific purposes.

It is an object of the present invention to provide a method and system of and for extracting or separating at least one phytochemical from plant material or a phytochemical composition by placing the material or composition in at least a partial vacuum which causes the volatization and/or precipitation of at least one phytochemical from the plant material or a phytochemical composition at a temperature below 100° C.

It is an object of the present invention to provide a method and system of and for extracting or separating at least one phytochemical from plant material or a phytochemical composition without causing adverse or undesired chemical alteration of the at least one phytochemical by applying or the introducing of heat to the plant material or a phytochemical composition at a temperature below 100° C.

These and other objects of the invention are achieved by providing a system to extract a phytochemical from plant material or a phytochemical composition comprising: a vacuum chamber configured to hold plant material or a phytochemical composition and to maintain a vacuum; an evacuation pump configured to create a vacuum within the vacuum chamber; and a collection chamber in fluid communication with the vacuum chamber; wherein when plant material or the phytochemical composition is placed in the vacuum chamber, the amount of vacuum created in the vacuum chamber by and with the evacuation pump is sufficient to cause at least one phytochemical to volatizes and/or precipitate from the plant material or the phytochemical composition and collect in the collection chamber without using a solvent, thereby creating a solvent-less phytochemical extract.

In certain embodiments, the inventive system further comprises a heat source, wherein the heat source increases the temperature within the vacuum chamber, wherein the vacuum chamber temperature is below 100° C., and wherein the temperature causes the volatilization of the at least one phytochemical.

In certain embodiments of the inventive system, at least one valve is included within the system to facilitate return of the vacuum chamber to ambient atmospheric pressure.

In certain embodiments of the inventive system, upon actuation of the at least one valve the collection chamber is recompressed.

In certain embodiments of the inventive system, the at least one valve enables an explosive return of the vacuum chamber to ambient atmospheric pressure.

In certain embodiments of the inventive system, the at least one valve enables explosive recompression of the plant material within the collection chamber.

In certain embodiments of the inventive system, a pressurized gas or air reservoir in fluid communication with the at least one valve is included, wherein upon actuation of the at least one valve the vacuum chamber is compressed to approximately the pressure of the pressurized gas or air reservoir.

In certain embodiments of the inventive system, a second evacuation pump in fluid communication with the collection chamber is included capable of evacuating the collection chamber when the evacuation pump in fluid communication with the vacuum chamber is actuated and creating at least a partial vacuum in the vacuum chamber.

In certain embodiments of the inventive system, a filter or trap is included wherein upon return of the vacuum chamber to ambient atmospheric pressure, the at least one phytochemical is collected in or with the filter or trap.

In certain embodiments of the inventive system, the plant material is from and belongs to the plant family Cannabaceae sensu stricto.

In certain embodiments of the inventive system, the phytochemical composition includes a cannabinoid.

In certain embodiments of the inventive system, the heat source comprises combustion of a fuel.

In certain embodiments of the inventive system, the heat source comprises an electrical heat element.

In certain embodiments of the inventive system, the heat source comprises a heated gas.

In certain embodiments of the inventive system, the heated gas is air.

In certain embodiments of the inventive system, the collected phytochemical includes a cannabinoid.

In certain embodiments of the inventive system, the solvent-less phytochemical extract belongs to the group consisting of cannabinoids, terpenes, or combinations thereof.

In certain embodiments of the inventive system, the heat source comprises an electrical heating element.

In certain embodiments of the inventive system, the collection chamber is located within or is part of the vacuum chamber.

In certain embodiments of the inventive system, the phytochemical collects in the collection chamber without using a solvent, thereby creating a solvent-less phytochemical extract.

In certain embodiments of the inventive system, the collection chamber and/or the trap or filter is cooled to a temperature below the temperature of the vacuum chamber to more effectively and efficiently collect the at least one phytochemical.

In certain embodiments of the inventive system, at least one processor, at least one memory, at least one software program, and at least one configurable hardware device in wired or wireless communication with at least one temperature sensor, at least one pressure and/or vacuum sensor, at least one valve control solenoid, and at least one temperature control solenoid is included to provide digital command and control of the system.

Objects of the invention are achieved by providing a method of and for extracting a phytochemical from plant material or a phytochemical composition, the method comprising the steps of: providing a vacuum chamber configured to hold plant material or a phytochemical composition and maintain a vacuum; providing an evacuation pump configured to create a vacuum within the vacuum chamber; providing a collection chamber in fluid communication with the vacuum chamber; wherein when plant material or a phytochemical composition is placed in the vacuum chamber, the amount of vacuum created in the vacuum chamber by and with the evacuation pump sufficient to cause at least one phytochemical to volatizes and/or precipitate from the plant material or phytochemical composition and collect in the collection chamber without using a solvent, thereby creating a solvent-less phytochemical extract.

In certain embodiments, the inventive method includes the further step of providing a heat source, wherein the heat source increases the temperature within the vacuum chamber, the vacuum temperature is below 100° C., and the temperature causes the volatilization of the at least one phytochemical.

In certain embodiments, the inventive method includes the further step of providing at least one valve within the system to facilitate return of the vacuum chamber to ambient atmospheric pressure.

In certain embodiments, the inventive method includes the further step of providing at least one valve enabling an explosive return of the vacuum chamber to ambient atmospheric pressure.

In certain embodiments, the inventive method includes the step of providing at least one valve enabling explosive recompression of the chamber.

In certain embodiments, the inventive method includes the further step of providing a pressurized gas or air reservoir in fluid communication with the at least one valve, wherein upon actuation of the at least one valve the vacuum chamber is compressed to approximately the pressure of the pressurized gas or air reservoir.

In certain embodiments, the inventive method includes the further step of providing a second evacuation pump in fluid communication with the collection chamber capable of evacuating the collection chamber when the evacuation pump in fluid communication with the vacuum chamber is actuated and thereby creating at least a partial vacuum in the vacuum chamber In certain embodiments, the inventive method includes the further step of providing a filter or trap wherein upon return of the vacuum chamber to ambient atmospheric pressure, the at least one phytochemical is collected in or with the filter or trap.

In certain embodiments of the inventive method, the plant material is from and belongs to the plant family Cannabaceae sensu stricto.

In certain embodiments of the inventive method, the phytochemical composition includes a cannabinoid.

In certain embodiments of the inventive method, the solvent-less phytochemical extract belongs to the group consisting of cannabinoids, terpenes, or combinations thereof.

In certain embodiments of the inventive method, the heat source comprises an electrical heating element.

In certain embodiments of the inventive method further comprising cooling the collection chamber and/or the trap or filter to a temperature below the temperature of the vacuum chamber to more effectively and efficiently collect the at least one phytochemical.

In certain embodiments of the inventive method, at least one processor, at least one memory, at least one software program, and at least one configurable hardware device in wired or wireless communication with at least one temperature sensor, at least one pressure and/or vacuum sensor, at least one valve control solenoid, and at least one temperature control solenoid is provided to enable digital command and control of the system.

Objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 3A-3B are schematic diagram depicting embodiments of the inventive method and system.

DETAILED DESCRIPTION OF THE INVENTION

In the following description, numerous details are set forth for the purpose of example and explanation; however, one of ordinary skill in the art will realize that the invention may be practiced without the use of these specific details.

Figure 1:
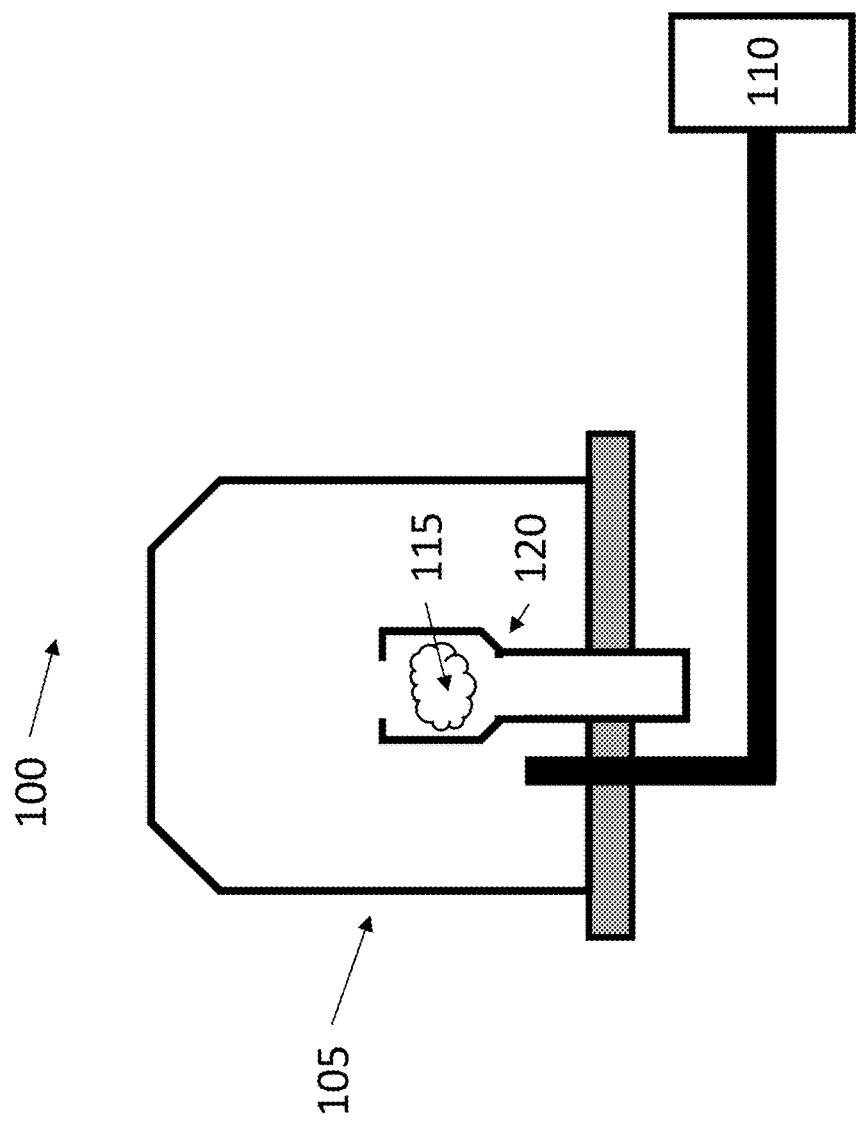
FIG. 1 is a schematic diagram depicting an embodiment of the inventive method and system.

As depicted in FIG. 1, in an embodiment of the inventive method and system (100), a vacuum chamber (105) configured for and capable of maintaining at least a partial vacuum is in fluid communication via a conduit with an evacuation pump (110). Plant material or a phytochemical composition (115) is placed in the vacuum chamber (105) and the evacuation pump (110) actuated to produce at least a partial vacuum in the vacuum chamber (105) adequate to cause volatization and/or precipitation of at least one phytochemical for collection.

It is contemplated that the plant material or phytochemical composition (115) may be placed and held in the vacuum chamber (105) by many and varied known methods or systems. For example, the plant material or phytochemical composition (115) may be placed on a base or plate, within a bowl or cradle, or other holder (120), or simply suspended within the vacuum chamber (105) as would be convenient with stemmed plants and/or stemmed flowering plants (Not Shown).

It is contemplated that phytochemical collection may comprise simply allowing the vacuum chamber (105) vacuum/pressure to eventually via the non-actuated evacuation pump (110) equalize and return the vacuum chamber to ambient atmospheric pressure (210), and then collecting the extracted phytochemical from the interior of the vacuum chamber (105).

Figure 2:
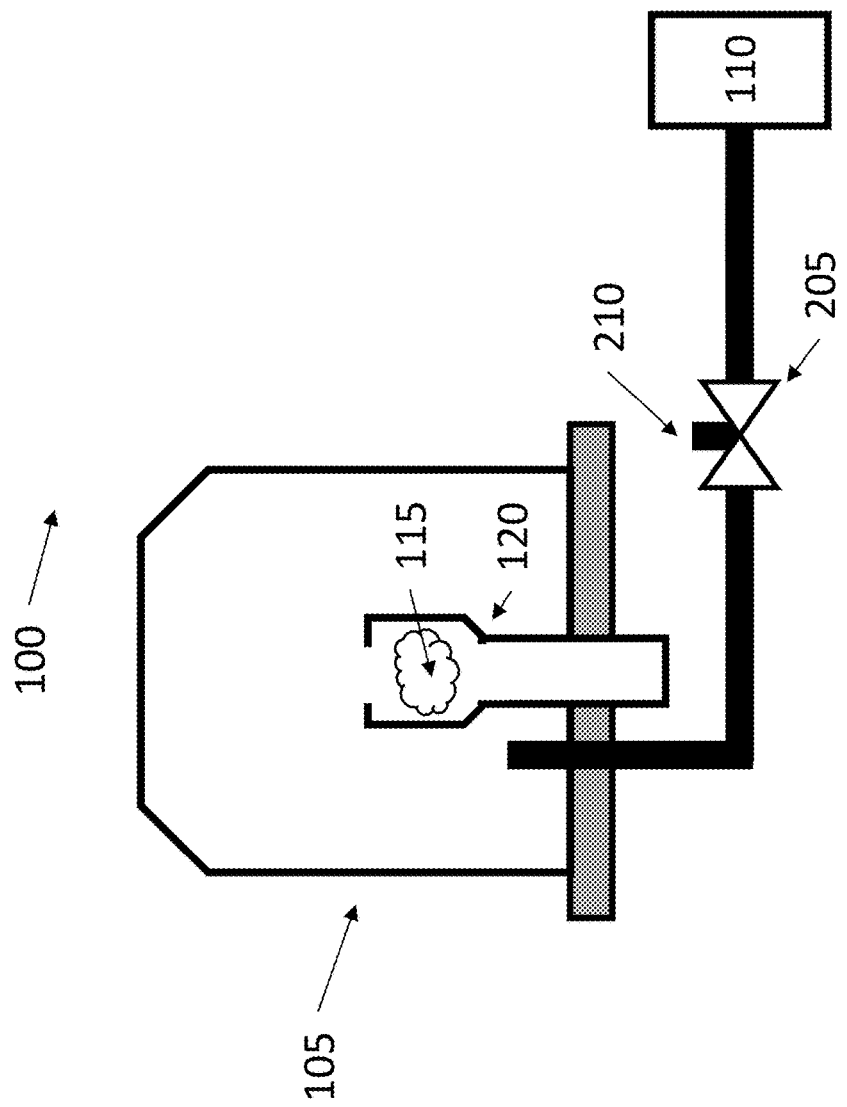
FIG. 2 is a schematic diagram depicting an embodiment of the inventive method and system.

As depicted in FIG. 2, it is contemplated that a valve (205) may be included within the system to facilitate returning the chamber (105) to ambient atmospheric pressure (210).

As depicted in FIG. 3A and FIG. 3B, it is contemplated that the method and system include a heat source (130) to increase the internal temperature of the vacuum chamber (105) and/or the temperature of the plant material or phytochemical composition (115) above ambient room temperature and thus increase volatilization of phytochemicals at a desired, selected, and/or provided partial vacuum.

It is contemplated that the temperature to which the heat source (130) increases the internal temperature of the vacuum chamber (105) and/or the temperature of the plant material or phytochemical composition (115) is below 100° C. to enable volatilization of a phytochemical at a lower vacuum without causing pyrolysis of the plant material or phytochemical composition (115).

It is contemplated that utilizing either controlled or explosive recompression of the chamber (105), the at least one phytochemical is collected via a collection chamber (305, 305'). In certain embodiments, the collection chamber (305, 305') may be located within the vacuum chamber (305), or may be separate from and in fluid communication with the vacuum chamber (305'). It is contemplated that the system (100) include a valve (205) capable of controlled and/or explosive venting of the vacuum chamber (105) to the ambient atmosphere (210).

It is contemplated that utilizing explosive recompression of the vacuum chamber (105), the at least one phytochemical is collected via the collection chamber (305, 305').

Figure 4A:
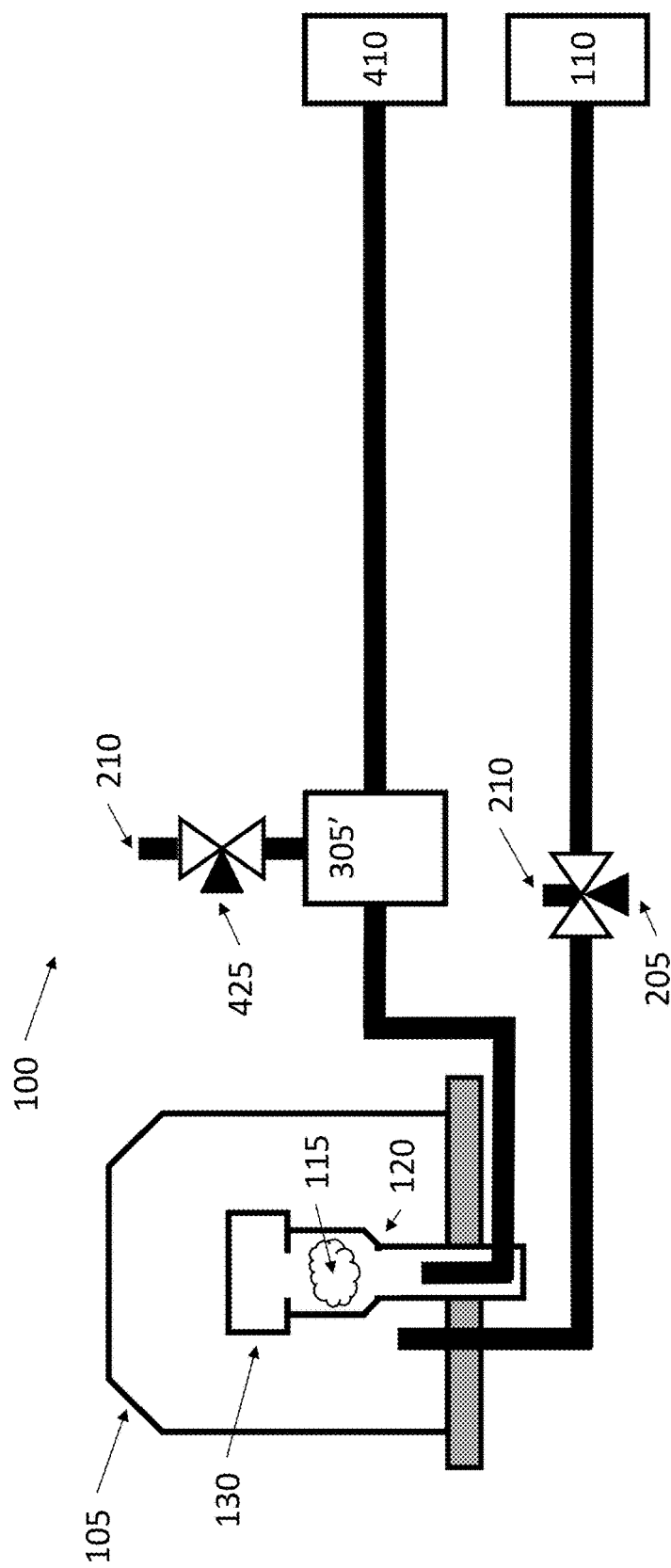
FIG. 4A-4H are schematic diagram depicting embodiments of the inventive method and system.

As depicted in FIG. 4A, it is contemplated that the inventive method and system (100) includes a second evacuation pump (410) capable of high-vacuum and high-velocity operation and in fluid communication with the collection chamber (305, 305'). It is contemplated that the system (100) include a valve (425) capable of controlled and/or explosive venting of the collection chamber (305, 305') to the exterior ambient atmosphere (210).

Figure 4B:
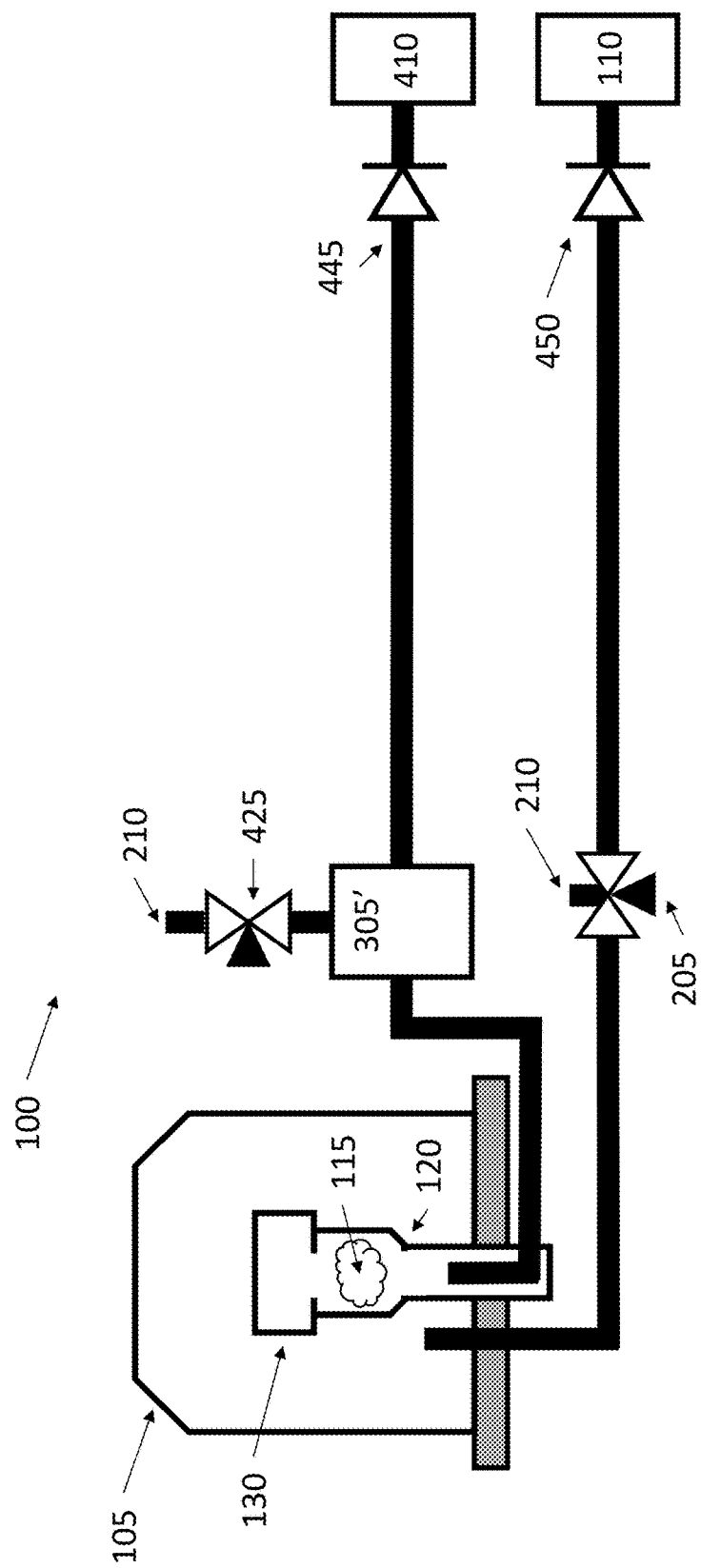

As depicted in FIG. 4B, it is contemplated that the inventive method and system (100) includes at least one check valve (445) capable of high-vacuum and high-velocity operation in fluid communication with the collection chamber (305, 305'), and the second evacuation pump (410) to facilitate maintaining a selected and desired vacuum within the vacuum chamber (105) and/or collection chamber (305, 305'). It is contemplated that the inventive method and system (100) includes a second check valve (450) capable of high-vacuum and high-velocity operation in fluid communication with the vacuum chamber (105) and the evacuation pump (110) to facilitate maintaining a selected and desired vacuum within the vacuum chamber (105) and/or the collection chamber (305, 305').

Figure 4C:
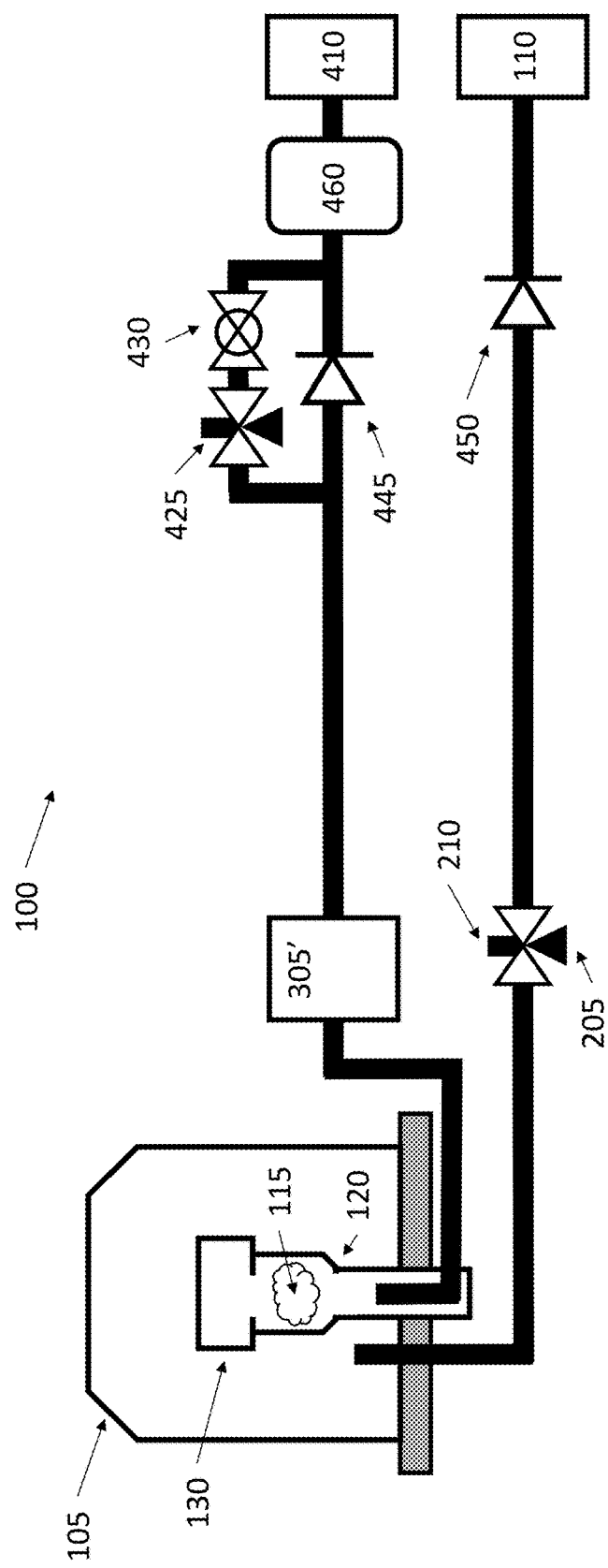

As depicted in FIG. 4C, it is contemplated that the inventive method and system (100) includes at least one ball or globe valve (430) capable of explosive operation or actuation in fluid communication with the collection chamber (305, 305'), a high-vacuum tank or reservoir (460), and the second evacuation pump (410). It is contemplated that an instantaneous or near-instantaneous vacuum source may be provided; the evacuation pump (110) providing and maintaining a selected or desired vacuum within the vacuum chamber (105) and/or collection chamber (305, 305') for volatizing and/or precipitating a phytochemical from plant material or a phytochemical composition (115); and that via the at least one ball or globe valve (430), the high-vacuum tank or reservoir (460) holding a vacuum greater than the vacuum in the vacuum chamber (105) and/or the collection chamber (305, 305') provided by the second evacuation pump (410). Once a selected period has elapsed after the selected or desired vacuum is achieved within the vacuum chamber (105) via the evacuation pump (110); the ball or globe valve (430) may be explosively opened to purge the system (100) and further collect at least one phytochemical (no shown) via the collection chamber (305 or 305').

Figure 4D:
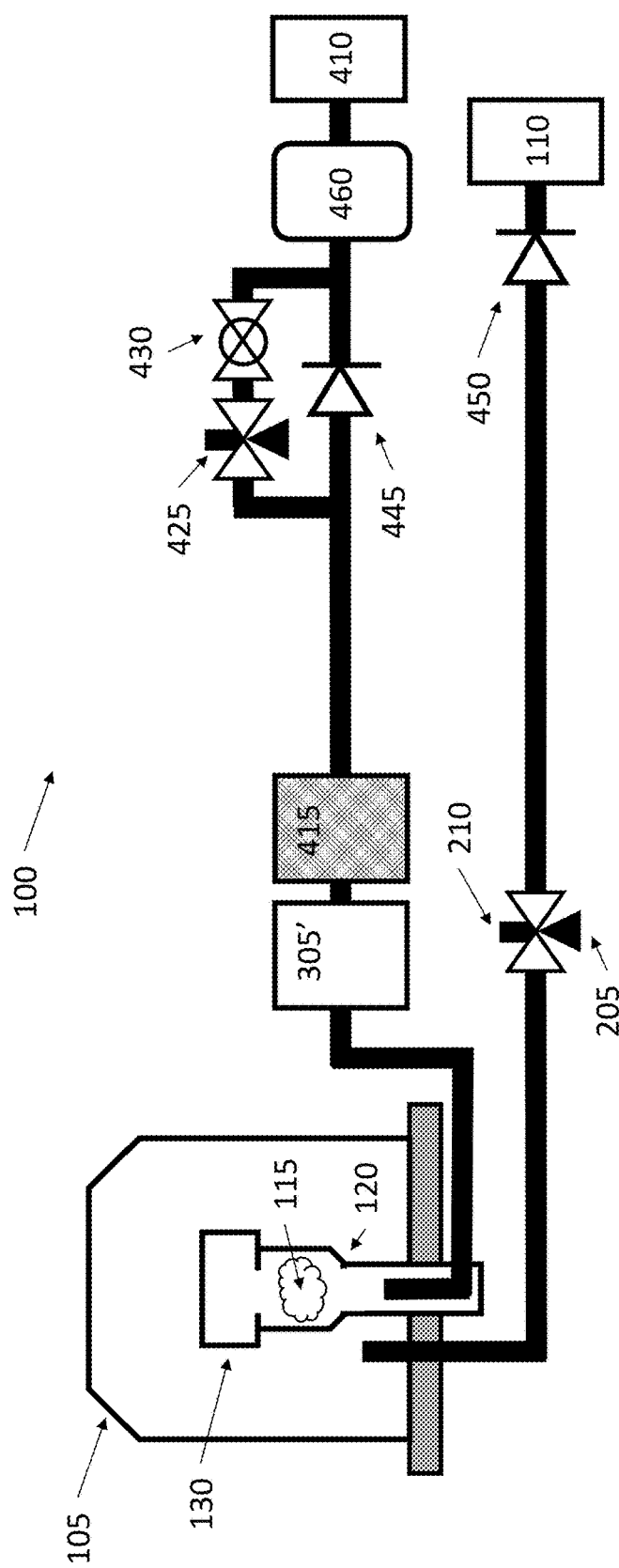

As depicted in FIG. 4D, it is contemplated that the inventive method and system (100) includes at least one trap or filter including a plurality of variably configured apertures (415) in fluid communication with the collection chamber (305, 305'), the high-vacuum tank or reservoir (460), and the second evacuation pump (410). As previously described above regarding FIG. 4C, utilizing the evacuation pump (110) to provide and maintain a selected or desired vacuum within the vacuum chamber (105) and/or collection chamber (305, 305') for volatizing and/or precipitating a phytochemical from plant material or a phytochemical composition (115); and that via the at least one ball or globe valve (430), the high-vacuum tank or reservoir (460) holding a vacuum greater than the vacuum in the vacuum chamber (105) and/or the collection chamber (305, 305') provided by the second evacuation pump (410); an instantaneous or near-instantaneous vacuum source is provided. Once a selected period has elapsed after the selected or desired vacuum is achieved within the vacuum chamber (105) via the evacuation pump (110); the ball or globe valve (430) may be explosively opened to purge the system (100) and further collect at least one phytochemical (not shown) via the collection chamber (305 or 305') and/or via the trap or filter (415).

It is contemplated that the trap or filter (415) may be remote from, and/or internal to or integral with (not shown), the collection chamber (305, 305'). It is also contemplated that the collection chamber (305, 305') and/or the trap or filter may be cooled to a temperature below the temperature of the vacuum chamber (105) to more effectively and efficiently collect a desired or selected phytochemical.

Figure 4E:
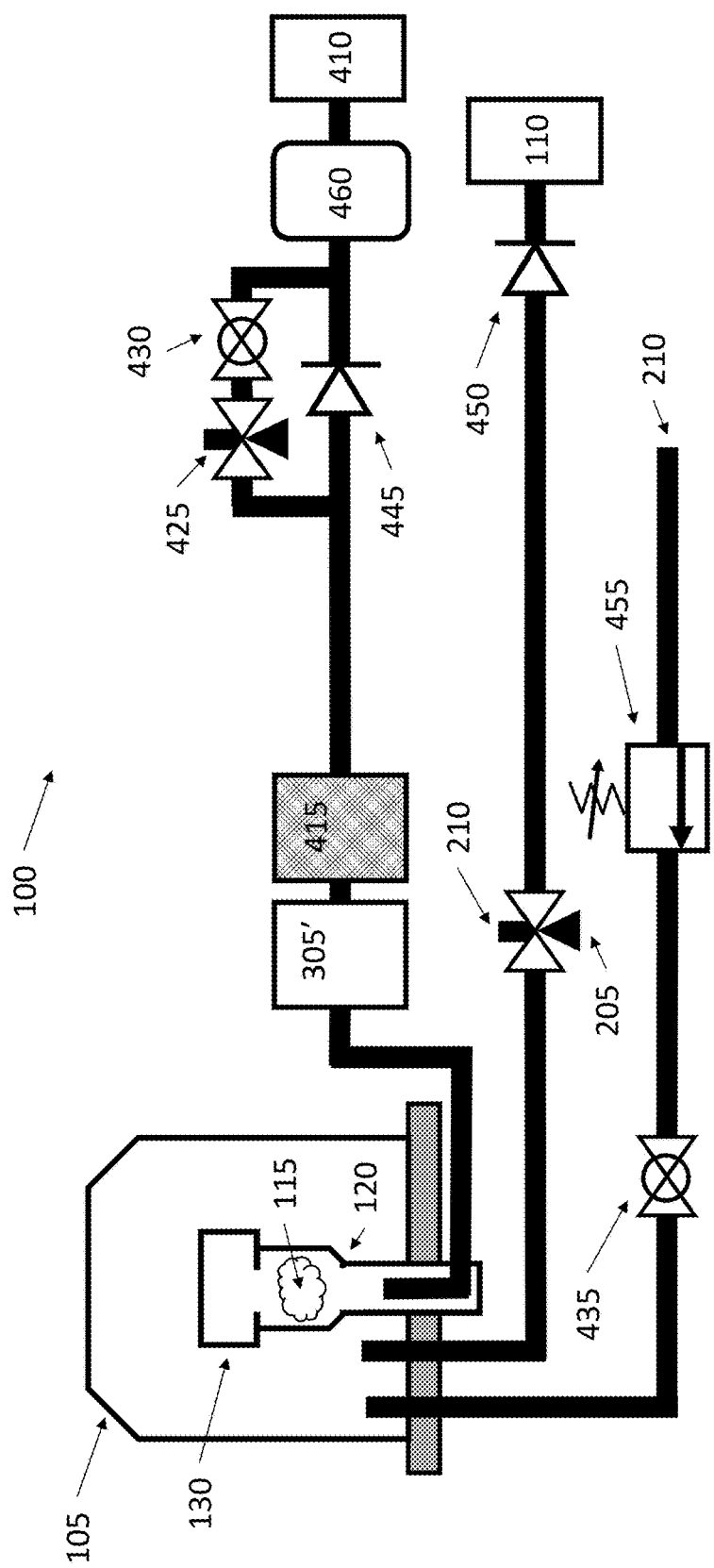

As depicted in FIG. 4E, it is contemplated that the inventive method and system (100) includes at least one variable vacuum/pressure regulator (455) in fluid communication with: the vacuum chamber (105), a second ball or globe valve (435), in fluid communication with the external ambient atmosphere (210). Similar to as previously described above regarding FIG. 4C and FIG. 4D; utilizing the evacuation pump (110) to provide and maintain a selected or desired vacuum within the vacuum chamber (105) and/or collection chamber (305, 305') for volatizing and/or precipitating a phytochemical from plant material or a phytochemical composition (115); and that via the at least one ball or globe valve (430), the high-vacuum tank or reservoir (460) holding a vacuum greater than the vacuum in the vacuum chamber (105) and/or the collection chamber (305, 305') provided by the second evacuation pump (410); an instantaneous or near-instantaneous vacuum source is provided. Once a selected period has elapsed after the selected or desired vacuum is achieved within the vacuum chamber (105) via the evacuation pump (110); the ball or globe valve (430) may be explosively opened to purge the system (100) and further collect at least one phytochemical (not shown) via the collection chamber (305 or 305') and/or via the trap or filter (415). It is contemplated that to prevent any extracted phytochemical from undesired reverse travel within the system (100), the second ball or globe valve (435) and the variable vacuum/pressure regulator (455) may be activated in a controlled manner to de- or re-compress the vacuum chamber (105) and/or collection chamber (305, 305').

Figure 4F:
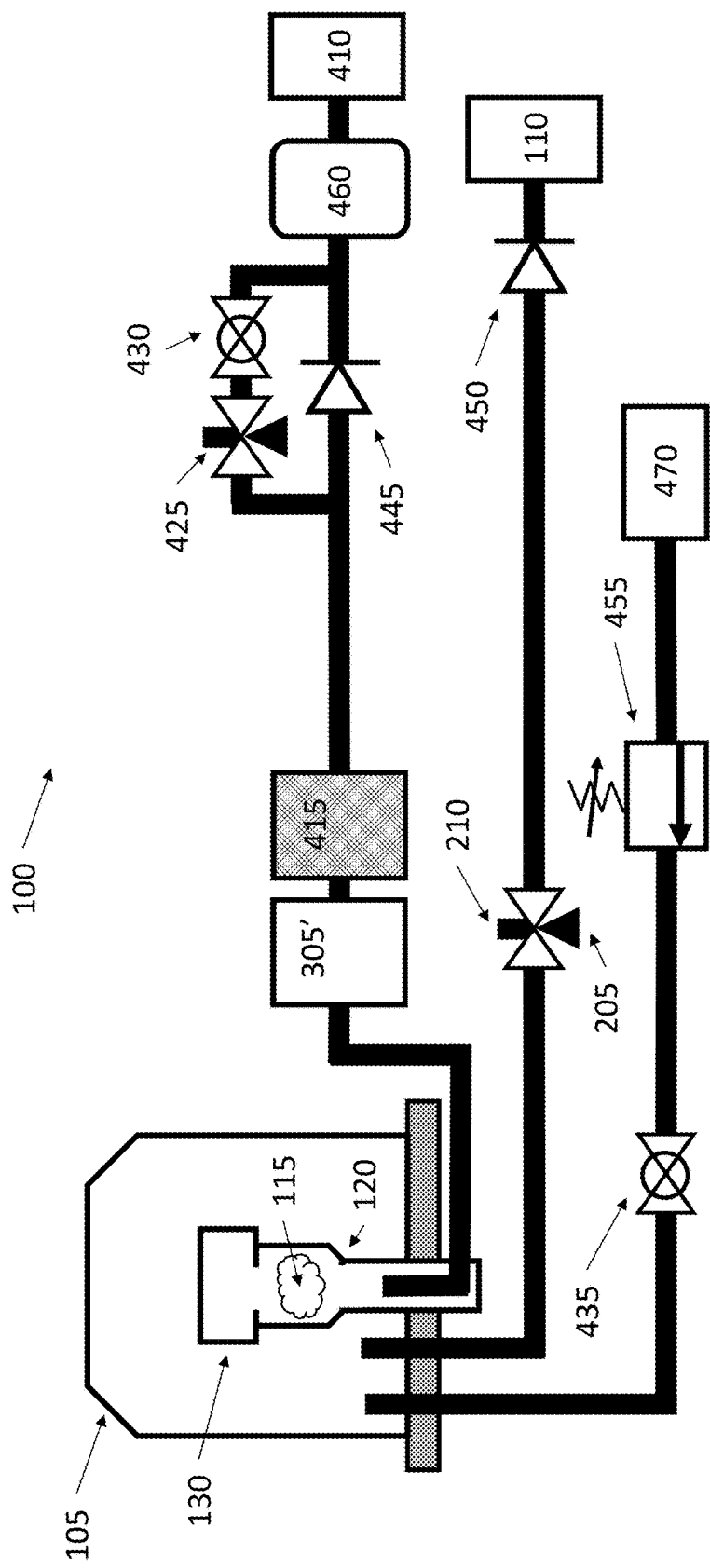

As depicted in FIG. 4F, in one embodiment of the inventive method and system, a pressurized gas or air reservoir (470) is provided and in fluid communication with the variable vacuum/pressure regulator (455), wherein instead of recompressing the vacuum chamber (105) to external ambient atmospheric pressure (210), actuation of the second ball or globe valve (435) explosively compresses and/or pressurizes the vacuum chamber (105) to the approximate gas or air pressure within the pressurized reservoir (470) dependent upon the setting of the variable vacuum/pressure regulator (455), thus more efficiently and effectively removing any extracted phytochemical from the surface of the material or composition, and/or from the interior of the system (100). Explosive compression of the chamber (110) to a pressure above ambient air pressure (210) further facilitates collection of the at least one phytochemical by stripping or dislodging and collecting the volatized and/or precipitated at least one phytochemical.

Figure 4G:
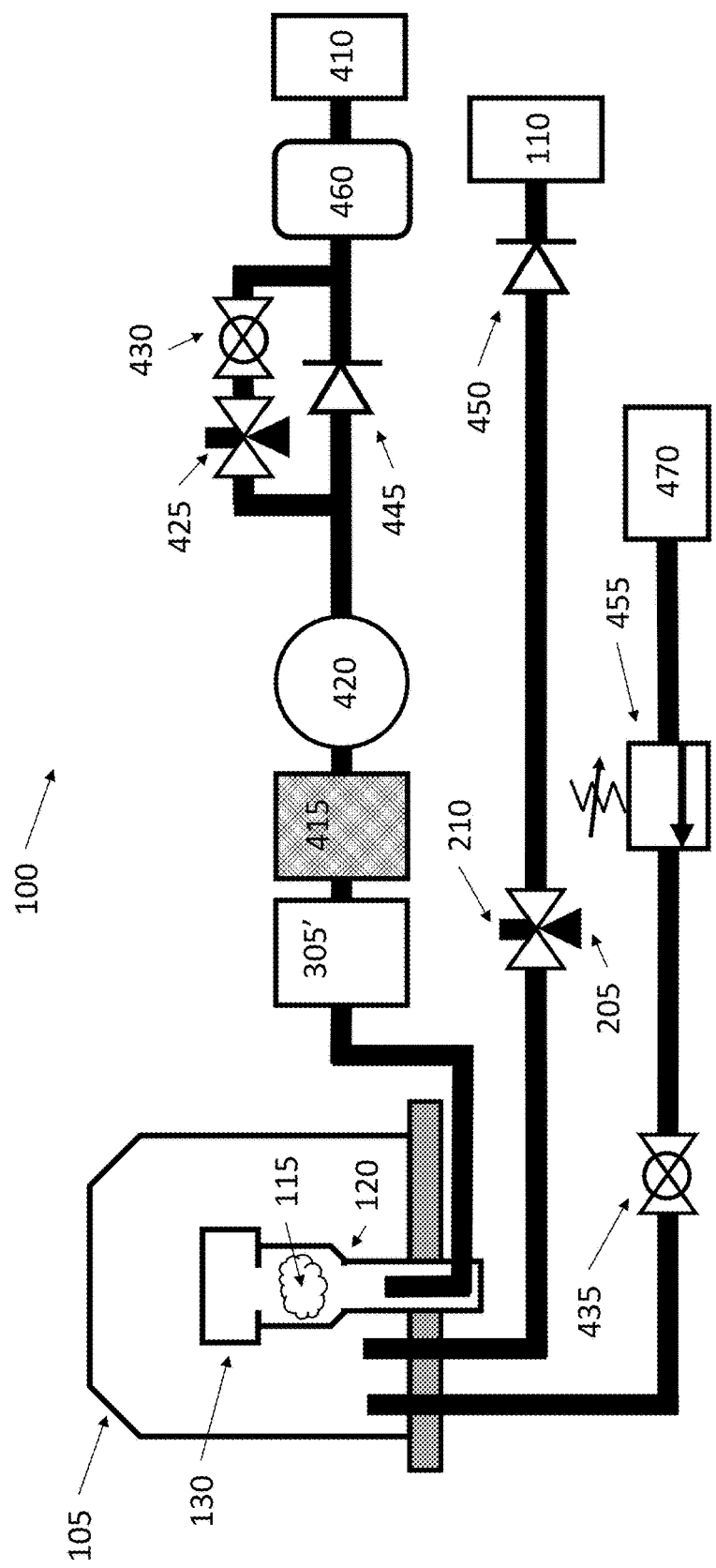

As depicted in FIG. 4G, in one embodiment of the inventive method and system (100) includes a known distillation and/or vacuum distillation step (420) of the phytochemical collected to substantially remove any solvent, ballast, fat, wax, carbohydrate, protein, sugar, and/or terpene therefrom the plant material or phytochemical composition (115).

Figure 4H:
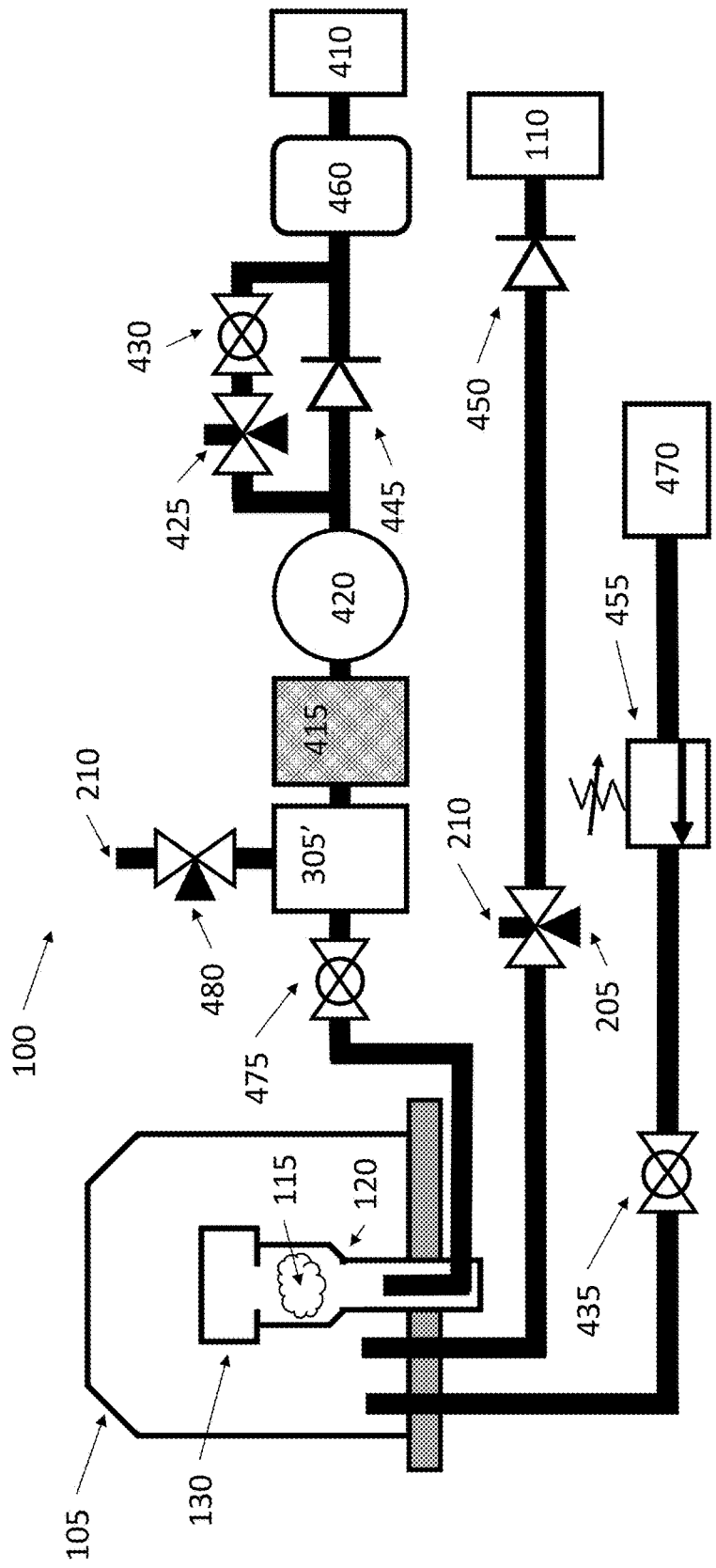

As depicted in FIG. 4H, in one embodiment of the inventive method and system (100) includes valves (475, 480) in fluid communication with the collection chamber (305, 305') and the ambient atmosphere (210). It is contemplated that with valve (475) open, valve (480) closed, and the vacuum chamber (105) under at least a partial vacuum; at least one phytochemical will collect in the collection chamber (305, 305'). As desired or selected, valve (475) is closed and valve (480) opened to more efficiently and effectively collect the at least one phytochemical via the filter or trap (415).

It is contemplated that the plant material (115) is from and belongs to the plant family Cannabaceae sensu stricto.

It is contemplated that the phytochemical composition (115) includes a cannabinoid.

It is contemplated that the heat source (130) comprises combustion of a fuel.

It is contemplated that the heat source (130) comprises an electrical heat element.

It is contemplated that the heat source (130) comprises a heated gas.

It is contemplated that the at least one phytochemical extracted and/or collected includes a cannabinoid.

It is contemplated that the at least one phytochemical extracted and/or collected includes a terpene.

It is contemplated that the plant material or phytochemical composition (115) be heated to a temperature below 100° C. to enable improved volatilization of the at least one phytochemical at a lower vacuum than as if no heat above the external ambient air temperature were provided.

It is contemplated that the vacuum chamber (105) and/or plant material or phytochemical composition (115) is heated to a temperature below 100° C. before evacuating the vacuum chamber (105).

It is contemplated that the vacuum chamber (105) and/or plant material or phytochemical composition (115) is heated to a temperature below 100° C. after evacuating the vacuum chamber (105).

It is contemplated that the vacuum chamber (105) and/or plant material or phytochemical composition (115) is heated to a temperature below 100° C. concurrently with evacuating the vacuum chamber (105).

Referring to the Figures, one theory of operational embodiment may be as follows. With the evacuation pump (110) disabled and the valve (205) open and located in the system (100) between the vacuum chamber (105) and the evacuation pump (110) as depicted, the plant material or a phytochemical composition (115) is placed in the vacuum chamber (105). It is contemplated that the vacuum chamber (105) is airtight and capable of maintaining a vacuum created and drawn therein by activation of the evacuation pump (110). It is also contemplated that the vacuum chamber (105) includes an opening and closing sealable door or port (Not Shown) to facilitate introduction and removal of the plant material or phytochemical composition (115) in and from the vacuum chamber (105).

Once the plant material or phytochemical composition (115) is placed inside the vacuum chamber (105), the valve (205) is adjusted to enable the evacuation of the vacuum chamber (105) when the evacuation pump (110) is activated thus creating at least a partial vacuum in the vacuum chamber (105). As the drawn vacuum increases, at least one phytochemical volatizes from and/or precipitates out of plant material or phytochemical composition (115) depending upon the dew-point temperature within the vacuum chamber (105). If the temperature of the vacuum chamber (105) interior walls is below the dew point for and in accordance with the amount of vacuum in the vacuum chamber (110), the at least one phytochemical will volatize and collect (i.e. cold condense) on the interior walls of the vacuum chamber (110). If the temperature of the vacuum chamber (110) interior walls is above the dew point for and in accordance with the amount of vacuum in the vacuum chamber (110), the at least one phytochemical precipitates out of the plant material or phytochemical composition and collects on the surface the material or composition.

It is contemplated that in the case of phytochemical volatilization, a filter or trap (415) be placed between the source of volatilization and the point of cold condensation for ease of phytochemical collection, for increased system and production efficiency, and for improved system cleaning and maintenance.

In certain embodiments, the filer or trap (415) is located within the collection chamber (305, 305').

It is contemplated that the inventive method and system (100) may include at least one processor, memory, software program, configurable hardware device, temperature sensor, pressure and/or vacuum sensor, valve control solenoid, temperature control solenoid, and/or other electromechanical system or device (none shown) to provide digital command and control of the inventive method and system.

It is contemplated that the inventive method and system (100) may include at least one processor, memory, software program, and configurable hardware device in wired or wireless communication with at least one temperature sensor, pressure and/or vacuum sensor, valve control solenoid, temperature control solenoid, and/or other electromechanical system or device (none shown) to provide remote digital command and control of the inventive method and system.

It is contemplated that the inventive method and system (100) may include at least one processor, memory, software program, and configurable hardware device in wired or wireless communication with at least one temperature sensor, pressure and/or vacuum sensor, valve control solenoid, temperature control solenoid, and/or other electromechanical system or device (none shown) to provide remote digital command and control of the inventive method and system via an intranet, Internet, or other communication network.

Additional details regarding the invention are referred to in the attached Appendix to the application.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

What is claimed is:

1. A method for preparing a phytochemical extract from Cannabaceae plant material comprising the steps of:
    (a) placing Cannabaceae sensu stricto plant material in a vacuum chamber configured to hold the plant material and maintain a vacuum;
    (b) applying a vacuum in the vacuum chamber by an evacuation pump to cause at least one phytochemical to volatize and/or precipitate from the plant material;
    (c) heating within the vacuum chamber and holding the temperature to below 100° C. via a heat source to cause the volatilization of the at least one phytochemical; and
    (d) collecting the at least one phytochemical in a collection chamber in fluid communication with the vacuum chamber;
    wherein said collection occurs without using a solvent, thereby obtaining the solvent-less phytochemical extract, and
        wherein the phytochemical is selected from the group consisting of cannabinoids, terpenes, and combinations thereof.

2. The method of claim 1, further comprising returning the vacuum chamber to ambient atmospheric pressure via at least one valve within the system.

3. The method of claim 2, wherein the at least one valve enables an explosive return of the vacuum chamber to ambient atmospheric pressure.

4. The method of claim 2, further comprising providing a pressurized gas or air reservoir in fluid communication with the at least one valve, wherein upon actuation of the at least one valve the vacuum chamber is compressed to approximately the pressure of the pressurized gas or air reservoir.

5. The method of claim 2, further comprising providing a second evacuation pump in fluid communication with the collection chamber capable of evacuating the collection chamber when the evacuation pump in fluid communication with the vacuum chamber is actuated and creating at least a partial vacuum in the vacuum chamber.

6. The method of claim 1, further comprising providing a filter or trap wherein upon return of the vacuum chamber to ambient atmospheric pressure, the at least one phytochemical is collected in or with the filter or trap.

7. The method of claim 1, further comprising cooling the vacuum chamber, the collection chamber and/or the trap or filter to a temperature below the dew-point of the of the volatized at least one phytochemical to more effectively and efficiently collect the at least one phytochemical.

8. The method of claim 1, wherein the heat source comprises an electrical heating element.

9. The method of claim 1, further comprising providing at least one processor, at least one memory, at least one software program, and at least one configurable hardware device in wired or wireless communication with at least one temperature sensor, at least one pressure and/or vacuum sensor, at least one valve control solenoid, and at least one temperature control solenoid to provide digital command and control of the method.

* * * * *